United States Patent
Gates et al.

(10) Patent No.: US 10,000,891 B2
(45) Date of Patent: *Jun. 19, 2018

(54) BIOMASS PROCESS OPTIMISATION

(71) Applicant: Bio-Sep Limited, Buckinghamshire (GB)

(72) Inventors: Malcolm Gilbert Gates, Buckinghamshire (GB); Anthony Robin McGarel-Groves, Buckinghamshire (GB); Nigel Donald Anderson, Buckinghamshire (GB); Kenneth John Coryton Day, Buckinghamshire (GB); Patrick Leahy, Buckinghamshire (GB); Geoffrey Nicholas Drage, Buckinghamshire (GB)

(73) Assignee: Bio-Sep Limited, Buckinghamshire (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/770,277

(22) PCT Filed: Feb. 26, 2014

(86) PCT No.: PCT/GB2014/050575
§ 371 (c)(1),
(2) Date: Aug. 25, 2015

(87) PCT Pub. No.: WO2014/132055
PCT Pub. Date: Sep. 4, 2014

(65) Prior Publication Data
US 2016/0002850 A1    Jan. 7, 2016

(30) Foreign Application Priority Data

Feb. 27, 2013 (GB) .................................. 1303520.9

(51) Int. Cl.
C07G 1/00 (2011.01)
D21C 11/00 (2006.01)
(Continued)

(52) U.S. Cl.
CPC ............ *D21C 11/0007* (2013.01); *C07G 1/00* (2013.01); *C07H 1/06* (2013.01); *D21C 1/04* (2013.01);
(Continued)

(58) Field of Classification Search
CPC ...... D21C 11/0007; D21C 1/04; D21C 3/003; D21C 3/20; D21C 3/224; C07G 1/00; C07H 1/06
See application file for complete search history.

(56) References Cited

U.S. PATENT DOCUMENTS 4,469,495 A * 9/1984 Hiraizumi .............. B01D 19/00
96/195
4,594,130 A    6/1986 Chang et al.
(Continued)

FOREIGN PATENT DOCUMENTS

CA    1284637 C * 6/1991
EP    2006354 A2    12/2008
(Continued)

OTHER PUBLICATIONS

Zhao, X., et al., "Organosolv pretreatment of lignocellulosic biomass for enzymatic hydrolysis," Appl. Microbiol. Biotechnol., 2009, 82, 815-827.*
(Continued)

*Primary Examiner* — Nicholas E Hill
(74) *Attorney, Agent, or Firm* — K&L Gates LLP (57) ABSTRACT

There is described a method of processing biomass which comprises the steps of: (i) processing biomass material in an aqueous system in the presence of an oxalic acid catalyst to produce a slurry; (ii) subjecting the slurry to an acidified organosolv liquor and optionally de-aerating the resulting mixture before exposing the mixture to ultrasound in a pretreatment step; and (iii) completing the fractionation
(Continued)

Overall process concept process using thermal digestion, followed by separation of the constituents into lignin, hemi-cellulose (monosaccharides) and cellulose with the addition of water.

18 Claims, 4 Drawing Sheets

(51) Int. Cl.
    *D21C 1/04*     (2006.01)
    *D21C 3/20*     (2006.01)
    *D21C 3/22*     (2006.01)
    *C07H 1/06*     (2006.01)
    *D21C 3/00*     (2006.01)

(52) U.S. Cl.
    CPC ............ *D21C 3/003* (2013.01); *D21C 3/20* (2013.01); *D21C 3/224* (2013.01)

(56) References Cited

U.S. PATENT DOCUMENTS

| | | | |
|---|---|---|---|
| 4,746,401 A * | 5/1988 | Roberts | D21C 3/222 162/72 |
| 5,730,837 A | 12/1998 | Black et al. | |
| 2005/0136520 A1 | 6/2005 | Kinley et al. | |
| 2010/0159516 A1 | 6/2010 | Diner et al. | |
| 2010/0287826 A1 * | 11/2010 | Hoffman | C10L 5/363 44/605 |
| 2016/0002851 A1 * | 1/2016 | Gates | D21C 1/00 530/507 |

FOREIGN PATENT DOCUMENTS

| | | | |
|---|---|---|---|
| EP | 2489780 A1 | 8/2012 | |
| WO | 79/00119 | 3/1979 | |
| WO | 2000/35579 A1 | 6/2000 | |
| WO | 2003/101577 A1 | 12/2003 | |
| WO | 2009/018469 A1 | 2/2009 | |
| WO | 2010/058185 A1 | 5/2010 | |
| WO | WO 2011039635 A2 * | 4/2011 | .............. C08H 8/00 |
| WO | WO 2011092711 A1 * | 8/2011 | .............. C13K 13/00 |

OTHER PUBLICATIONS

Bozell, Joseph J. et al., "Solvent fractionation of renewable woody feedstocks: Organoslov generation of biorefinery process streams for the production of biobased chemicals", Biomass and Bioenergy, vol. 35, (2011), pp. 4197-4208.

* cited by examiner

FIG. 1
Overall process concept

FIG. 2

Cumulative fractionation of each stage for oak with oxalic acid compared to an equivalent experiment with sulphuric acid (SA).

FIG. 3

Ternary phase diagram

FIG. 4
Overall process concept

FIG. 5

HPLC refractive index chromatograms of aqueous fractions for all feedstocks against a reference hemi-cellulose sample

BIOMASS PROCESS OPTIMISATION

CROSS REFERENCE TO RELATED APPLICATIONS

This is the national phase under 35 U.S.C. § 371 of International Application No. PCT/GB2014/050575, filed on Feb. 26, 2014, which claims priority to and the benefit of United Kingdom Patent Application No. 1303520.9, filed on Feb. 27, 2013, the entire disclosures of each of which are incorporated by reference herein.

FIELD OF THE INVENTION

The present invention relates to novel processes for the treatment of biomass materials.

In particular the invention relates to processes for the fractionation of various lignocellulosic feedstocks to their base components, i.e. cellulose, hemi-celluloses and lignin, with the use of an acid catalyst, a novel organosolv reagent and sonication.

BACKGROUND OF THE INVENTION

Most plant biomass materials, such as wood, are referred to as lignocellulosic material and comprise three main components, namely, cellulose, hemi-cellulose and lignin.
Cellulose: is a polysaccharide consisting of a linear chain of β(1→4) linked D-glucose units and will usually comprise 7,000 to 15,000 glucose molecules.
Hemi cellulose: is a polysaccharide related to cellulose but is derived from several sugars including glucose, xylose, mannose, galactose, rhamnose and arabinose and consists of shorter chains of around 200 sugar units.
Lignin is: a cross-linked macromolecule with molecular masses in excess of 10,000 and is relatively hydrophobic and aromatic in nature. Lignin is rich in the phenylpropanoids, such as p-coumaryl alcohol, coniferyl alcohol and sinapyl alcohol.

U.S. Pat. No. 5,730,837 describes the use of sulphuric acid in a 24% water, 44% methyl isobutyl ketone and 32% ethanol in the separation of biomass at 140° C. and resulting in an 18% yield of lignin based on the wood charged.

More recently, our co-pending International patent application PCT/GB2009/002731 describes a method of processing biomass which comprises the digestion of biomass material in an acidic aqueous medium, subjected to ultrasonic waves and separating the biomass into its constituents of lignin, hemi-cellulose and cellulose. This application describes the use of a variety of different acids, including an aliphatic dicarboxylic acid.

We have now found that, inter alia, the use of one particular acid, namely, oxalic acid, is advantageous in the treatment of biomass material in a pre-treatment stage and also in a subsequent digestion stage. We have also found a novel organosolv reagent which is suitable for the extraction of lignin and hemi-cellulose (monosaccharides) from biomass.

SUMMARY OF THE INVENTION

Figure 1:
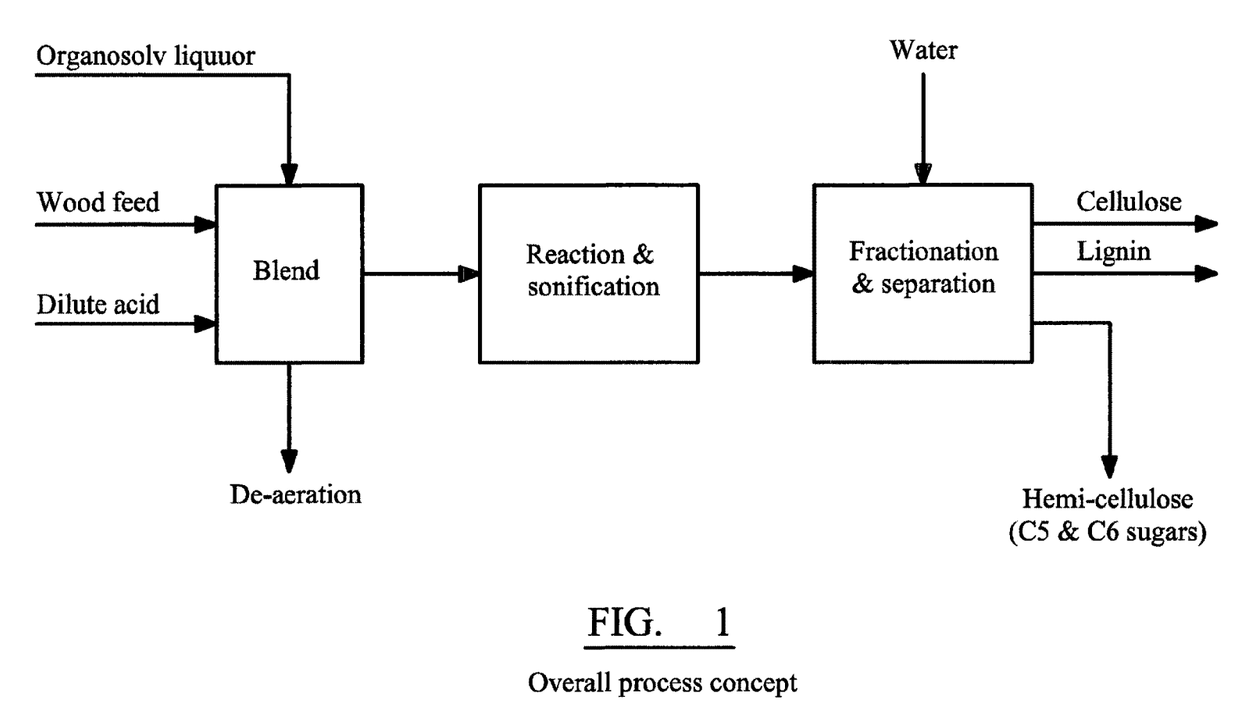
FIG. 1 illustrates the overall method of processing biomass according to the present invention.

The overall method of processing biomass according to the present invention is illustrated in FIG. 1. A biomass feed is added to dilute oxalic acid and blended to a slurry. The person skilled in the art will understand that the term "slurry" should not be deemed to be limiting. Thus, the term "slurry" shall mean a fluid mixture of a solid with a liquid, e.g. water or aqueous acid, which behaves like a thick fluid, for example, flowing under gravity and being capable of being pumped, etc. At the mixing stage the slurry is further mixed with an acidified organosolv reagent and the whole is de-aerated, e.g. with an inert gas, such as nitrogen, with or without the aid of sonication. In one embodiment of the present invention the de-aeration is carried with the aid of sonication. In another embodiment of the present invention the de-aeration is carried without the aid of sonication. The mixture or slurry is then sonicated in a pre-treatment stage. This energy input from the sonication enables the components of the lignocellulosic mixture to achieve maximum fractionation during the subsequent digestion stage, e.g. thermal digestion, into the components cellulose, lignin and hydrolysed hemi-cellulose (monosaccharides). The fractionated digested mixture is separated with the addition of, for example, water. The overall method of processing biomass according to the present invention is illustrated in FIG. 1.

Therefore, according to a first aspect of the invention there is provided a method of processing biomass which comprises the steps of:
(i) processing biomass material in an aqueous system in the presence of an oxalic acid catalyst to produce a slurry;
(ii) subjecting the slurry to an acidified organosolv liquor and optionally de-aerating the resulting mixture, e.g. with an inert gas, such as nitrogen, with or without the aid of sonication, before exposing the mixture to ultrasound in a pre-treatment step; and
(iii) completing the fractionation process using thermal digestion, followed by separation of the constituents into lignin, hemi-cellulose (monosaccharides) and cellulose with the addition of water.

The biomass processing step of step (i) hereinbefore described may comprise the pre-digestion of the biomass material. While the thermal digestion in step (iii) may comprise either a) the use of conventional systems employing moderate temperatures and pressure and residence time in the autoclave; or b) the use of even lower temperatures and pressure as well as residence time of being subjected to ultrasound.

In one embodiment of the present invention the optional step of de-aeration is carried with the aid of sonication. In another embodiment of the present invention the optional step of de-aeration is carried without the aid of sonication.

The amount of oxalic acid present may vary depending upon, inter alia, the nature of the biomass being processed.

A range of organic acids varying in acidity were trialled (see Example 1, Table 1).

Bozell, Joseph J et al "Solvent fractionation of renewable woody feedstocks: Organosolv generation of biorefinery process streams for the production of biobased chemicals" Biomass and Bioenergy (2011) 35, 4197-4208, describe the use of various acids in the digestion of biomass, including formic acid, acetic acid and peroxyformic acid, and especially sulphuric acid.

Of these, oxalic acid (ethanedioic acid) has been found to be of suitable digestive strength and environmental impact. Oxalic acid is a relatively weak acid, but has been shown to perform well in preparing the biomass at the blending stage and somewhat comparable to that of the stronger organic acids. Furthermore, the use of oxalic acid as an alternative to strong conventional mineral acids is advantageous since, inter alia, it avoids the use and cost of strong bases to neutralise the resultant liquors; avoids post-filtration steps; etc. Furthermore, oxalic acid does not inhibit glycolysis and does not produce noxious odours during any pre-treatment.

Oxalic acid is more expensive than, for example, sulphuric acid on a weight basis and therefore would not be an obvious choice of acid catalyst. However, oxalic acid is a solid at room temperature (melting point 189-191° C.) and can therefore be recovered and reused in an efficient and clean manner through simple crystallisation and filtration, or through chromatographic separation. In addition, oxalic acid has a high solubility in water (around 143 g/L at 25° C.).

The concentration of oxalic acid may be varied. Thus, for example, the concentration of oxalic acid may be from about 0.01M to about 1M, about 0.01M to about 0.5M, about 0.02M to about 0.4M, about 0.03M to about 0.3M, about 0.04M to about 0.2M, about 0.05M to about 0.1M. Preferably, the concentration of oxalic acid is about 0.05M, more preferably about 0.1M.

The ratio of dilute oxalic acid to biomass may vary depending upon, inter alia, the nature of the biomass, the concentration of the oxalic acid, etc. In the present invention various ratios of the biomass feed stock and dilute oxalic acid mixture were trialled within the blending stage to generate slurry of good homogeneity for downstream applications. With a dilute acid composition comprising 0.1M oxalic acid, it has been found that with woody saw dust a weight based ratio of from about 1:1 to about 1:10, e.g. about 1:5 biomass to dilute oxalic acid gave a good homogeneous medium. With a grassy biomass a weight based ratio of from about 1:1 to about 1:20, e.g. about 1:10 biomass to dilute oxalic acid yielded a similar result.

Wheat and palm frond, likely due to their absorptive nature, retain a higher amount of water compared to that of hardwoods, such as oak or softwoods, such as pine.

Therefore, the method of the present invention may be subdivided into a method of processing hardwood/softwood or a method of processing grasses, cereals or leaves. When the method of the present invention comprises the processing of hardwood, such as oak, or softwood, such as pine, the weight based ratio of biomass to dilute oxalic acid may be from about 0.1:10 to about 1:10, from about 0.2:10 to about 1:9, from about 0.4:10 to about 1:8, from about 0.6:10 to about 1:7, from about 0.8:10 to about 1:6, preferably about 1:5.

When the method of the present invention comprises the processing of grasses, cereals or leaves, the weight based ratio of biomass to dilute oxalic acid may be from 0.1:10 to about 1:20, from about 0.2:10 to about 1:18, from about 0.4:10 to about 1:16, from about 0.6:10 to about 1:14, from about 0.8:10 to about 1:12, preferably about 1:10.

In the process of the present invention, once the biomass has been blended with dilute oxalic acid to produce a slurry, the slurry can be mixed with an acidified organosolv liquor, de-aerated, e.g. with nitrogen, with or without the aid of sonication, and reacted, i.e. sonicated (it is desirable that the acid concentration of the entire system is kept constant, for example, at. 0.1M, at the entry point of the reaction and sonication stage, otherwise the final acid content may be diluted).

According to a yet further aspect of the invention the reaction/sonication step hereinbefore described is desirably conducted in an inert atmosphere.

The use of such an inert atmosphere in the processing of biomass is novel per se.

Thus, according to this aspect of the invention there is provided a method of processing biomass which comprises the steps of:
(i) processing biomass material in an inert atmosphere in an aqueous system in the presence of an oxalic acid catalyst to produce a slurry;
(ii) subjecting the slurry to ultrasound in a pre-treatment step; and
(iii) separating the biomass material into its biomass constituents of lignin, hemi-cellulose (monosaccharides) and cellulose.

This method of treatment with organosolv in the presence of an oxalic acid catalyst may optionally comprise a pre-treatment strategy that utilises organic solvent mixtures with water for the removal of lignin and concurrent hydrolysis of the hemi-cellulose for improved subsequent enzymatic hydrolysis of the cellulose fraction. In addition, the oxalic acid is utilised to hydrolyse hemi-cellulose.

Figure 2:
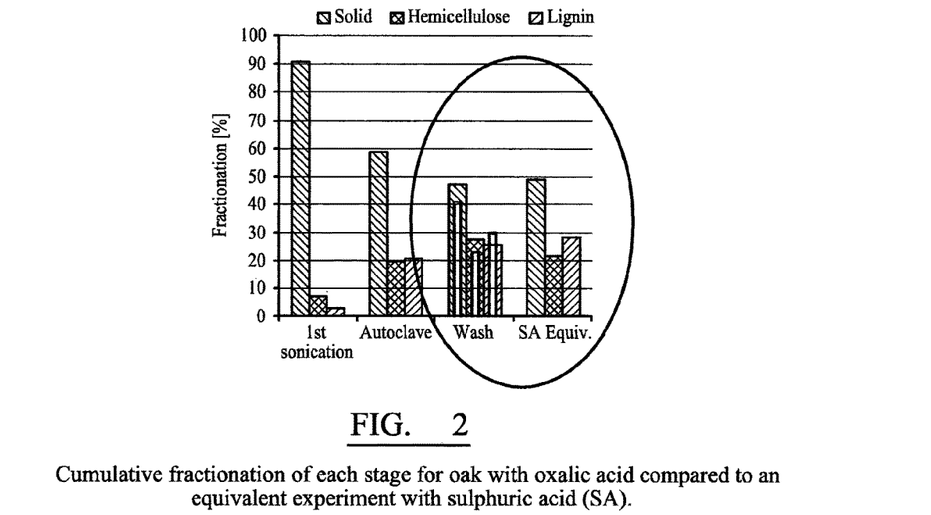
FIG. 2 illustrates the cumulative fractionation of each stage for oak with oxalic acid compared to an equivalent experiment with sulphuric acid.

FIG. 2 highlights the cumulative fractionation of each of the three key stages. It is clear to see that all stages have merit in their respective applications. A comparison against the results achieved with sulphuric acid (using an organosolv ratio of 44:32:24 wt. % MIBK:EtOH:$H_2O$) indicates a very similar yield in final pulp mass. This process (with oxalic acid as the catalyst) achieves a greater hemi-cellulose extraction and comparable lignin yields.

Analysing the aqueous fraction of like-for-like oxalic acid and sulphuric acid experiments within a pressurised system, i.e. in an autoclave indicates that the use of the oxalic acid aids the release of greater xylose quantity. However, with sulphuric acid, there is also a significant increase in the formation of degradation products, succinic acid and lactic acid in particular compared to the use of oxalic acid (see Example 5).

In summary, it is seen that the use of oxalic acid has greater efficiency in fractionating the biomass to the use of sulphuric acid, i.e. 80% to 70%.

The use of sulphuric acid as disclosed on the prior art, is a concern when scaling-up with regard to its corrosive nature and poor environmental credentials. The use of oxalic acid as an acid catalyst (to that of a mineral equivalent) has been shown not to leach any metal ions from an ultrasound reactor or autoclave, which may be fabricated from, for example, 316-stainless steel (molybdenum-bearing grade). This emphasises the apparent low corrosion impact on equipment possessed by oxalic acid.

A further advantage offered by the used of oxalic acid is the provision of a novel organosolv reagent. Organosolv reagents are known. For example, our co-pending International patent application PCT/GB2009/002731 and U.S. Pat. No. 5,730,837 both describe biomass extraction using an organosolv comprising 24% w/w water, 44% w/w methylisobutylketone (MIBK) and 32% w/w ethanol in 0.05 mol/L sulphuric acid ($H_2SO_4$). Bozell, J. J., et al in "Solvent fractionation of renewable woody feedstocks: Organosolv generation of biorefinery process streams for the production of biobased chemicals" available at www.sciencedirect.com describes the use of an organosolv ratio comprising MIBK:EtOH:$H_2O$ of 16:34:50 sulphuric acid catalyst.

According to a further aspect of the present invention there is provided an organosolv reagent comprising a ketone, such as, methylisobutylketone (MIBK); an alcohol, such as ethanol; and aqueous oxalic acid.

Thus, according to a preferred aspect of the present invention there is provided an organosolv reagent comprising methylisobutylketone (MIBK), ethanol and aqueous oxalic acid.

In the organosolv of this aspect of the invention the ketone may be an aliphatic ketone. Preferably the ketone is an aliphatic ketone having at least 4 carbon atoms (and may have as many as 10 carbon atoms). Aliphatic ketones which may be mentioned include, for example, methyl ethyl ketone, methyl isopropyl ketone, methyl propyl ketone, methyl butyl ketone, methyl isobutyl ketone, methyl isoamylketone, diethyl ketone, ethyl isopropyl ketone, ethyl propyl ketone, and ethyl isobutyl ketone. A particular ketone which may be mentioned is methyl isobutyl ketone (MIBK).

The alcohol may have less than about 4 carbon atoms to assure that it will be water-miscible. Useful alcohols which may be mentioned include, for example, methanol, ethanol, propanol, isopropanol and butanol. A preferred alcohol is ethanol.

Pre-treatment of biomass with acid, organic solvents and de-aeration facilitates selective digestion and separation of each component. In the present invention a ketone, such as, methyl isobutyl ketone (MIBK); and an alcohol, such as, ethanol (EtOH), are combined with aqueous oxalic acid ($H_2C_2O_4 \cdot H_2O$), making up the ternary phase diagram, see FIG. 3. (Note that since, in practice, the oxalic acid is dilute (preferably about 0.05M or about 0.1M) the phase diagram for MIBK/ethanol/aqueous oxalic acid is considered to closely resemble the phase diagram for MIBK/ethanol/water (shown in FIG. 3)).

Figure 3:
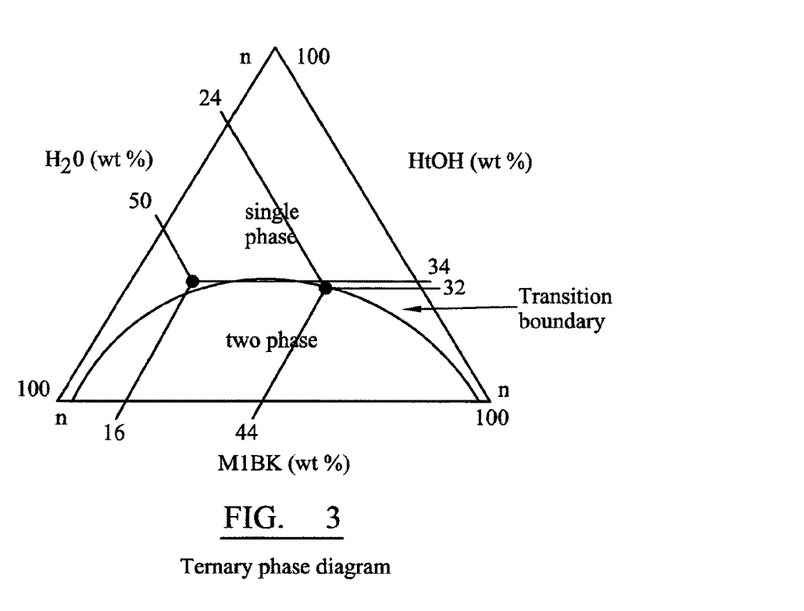
FIG. 3 illustrates the ternary phase diagram for MIBK; ethanol and aqueous oxalic acid ($H_2C_2O_4.H_2O$)

This figure highlights the phase (i.e. two or single) of the resultant mixture upon any combination of the three components that the mixture is made up of, i.e. MIBK, EtOH and $H_2C_2O_4 \cdot H_2O$. MIBK retains the soluble lignin, whereas the $H_2C_2O_4 \cdot H_2O$ captures the released soluble hemi-celluloses. Experiments with and without EtOH highlighted its inclusion as a phase transfer agent for the hemi-celluloses to the aqueous fraction.

Two mixture ratios have been extensively explored, namely 44:32:24 and 16:34:50 (wt. %) ratios of MIBK:EtOH:$H_2C_2O_4 \cdot H_2O$. These two ratios are on opposing sides of the phase transition curve and are chosen as both have shown to be of single phase through all pressures and temperatures of the fractionation. The organosolv reagent of 44:32:24 performed well in providing a solvent medium for lignin compounds, however it consistently resulted in a three-phase enriched hemi-cellulose/lignin solution thus being difficult to handle in the post fractionating steps.

The person skilled in the art will understand that the ratios of MIBK, EtOH and $H_2C_2O_4 \cdot H_2O$ may be varied. In a preferred aspect of the invention the ratios of ketone, alcohol and aqueous oxalic acid, in particular, the ratios of MIBK, EtOH and $H_2C_2O_4 \cdot H_2O$ are desirably such that in the organosolv reagent falls within the single phase of the above phase diagram. Specific, non-limiting, ratios of organosolv that may be mentioned are MIBK:EtOH:$H_2C_2O_4 \cdot H_2O$ 44:32:24 and 16:34:50.

According to a yet further aspect of the invention there is provided the use of an organosolv comprising a ketone, such as, methylisobutylketone (MIBK); an alcohol, such as ethanol; and aqueous oxalic acid in the selective separation of cellulose, hemi-cellulose and lignin from biomass material.

The use according to this aspect of the invention may comprise a pre-treatment (with sonication) step under de-aeration conditions.

The organosolv reagent can be added to the biomass and reacted. Once the reaction is complete, a solid/liquid separation is carried out before a predetermined amount of water is added to the resultant liquor to induce formation of separate organic and aqueous fractions. In the presence of increased ketone, e.g. MIBK, concentrations, the separation is generally (from bottom to top) an aqueous phase containing hemi-celluloses (monosaccharides), an isolated hydrophobic lignin layer and an organic fraction predominantly consisting of ketone, e.g. MIBK. The organic layer contains trace amounts of lignin and it is desirable to minimise this. Therefore, an organosolv ratio of 16:34:50, as hereinbefore described, is most preferred. A further benefit of this ratio is the ability to appropriately utilise the water passed on from the blending stage to make up the 50 wt. % required for full effectiveness of the organosolv assisted pre-treatment method.

In a preferred method of the invention the solvents ketone, e.g. MIBK, and alcohol, e.g. EtOH, are pre-mixed and added to blended slurry of aqueous oxalic acid and biomass at a ratio specified in Example 3, Table 3 in the presence of a de-aerated mixture. This composition conforms to the desired ratio of 1 g biomass to 10 ml organosolv solvents. The slurries at these ratios, are very fluid and easily transportable. This is especially true for the hard and softwoods. Biomass of a more fibrous nature is more absorbent and therefore an increased solvent ratio may be required.

According to a yet further aspect of the invention there is provided a method of processing biomass which comprises the steps of:
(i) processing biomass material in an aqueous system in the presence of an oxalic acid catalyst to produce a slurry;
(ii) subjecting the slurry to ultrasound in a pre-treatment step; and
(iii) separating the biomass material into its constituents of lignin, hemi-cellulose (monosaccharides) and cellulose using an organosolv reagent comprising a ketone; an alcohol; and aqueous oxalic acid.

Figure 4:
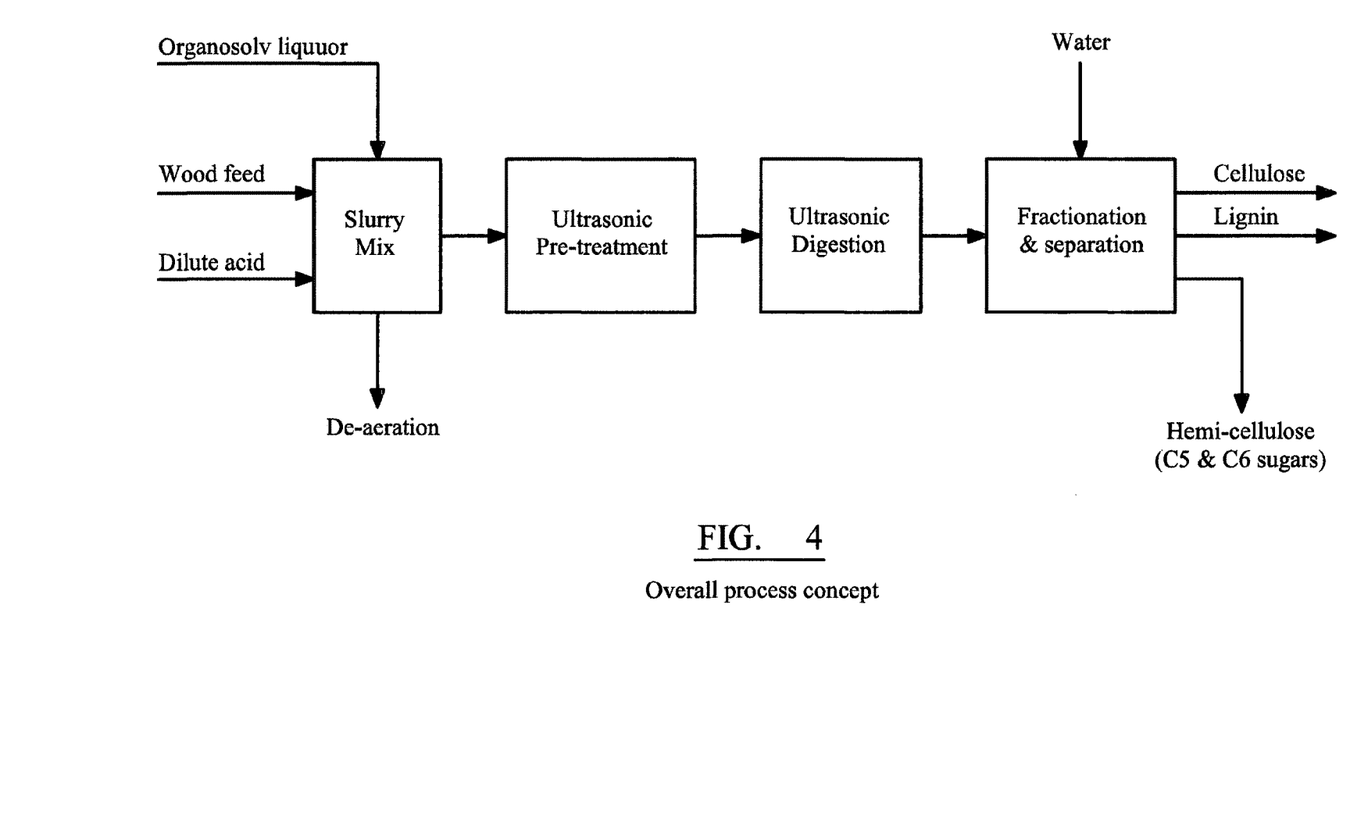
FIG. 4 illustrates the method of processing biomass according to the present invention including an ultrasound pre-treatment step.

The method of processing biomass according to this aspect of the invention including an ultrasound pre-treatment step is illustrated in FIG. 4.

Preferably, the method of this aspect of the invention comprises separating the biomass into its constituents of lignin, hemi-cellulose (monosaccharides) and cellulose using an organosolv reagent comprising a ketone; an alcohol; and aqueous oxalic acid, as hereinbefore described.

The inert atmosphere may be at ambient pressure, i.e. 1 atm or it may at an elevated pressure, e.g. a pressurised system, such as an autoclave, under an inert atmosphere. It will be understood by the person skilled in the art that a variety of inert gasses may be suitable for creating a suitable inert atmosphere. Non-limiting examples of such inert gases include, a noble gas, such as, argon, helium, krypton, neon and xenon; or nitrogen and mixtures thereof. A preferred inert gas is nitrogen.

As hereinbefore described the use of ultrasonication is beneficial in the hydrolysis of the hemi-celluloses present in the biomass. It is understood that the proton from the oxalic acid acts as a catalyst for the hydrolysis of the hemi-cellulose. The ultrasound provides the "mechanical" means to exercise the maximum exposure of the protons ($H^+$ ions) required for hydrolysis. Thus, ultrasonication may be used as a pre-treatment prior to applying other processes to the biomass material. Ultrasonication is beneficial in the hydrolysis of the hemi-celluloses to monosaccharides, the aldopentoses, such as, ribose, arabinose, xylose and lyxose. Such monosaccharides are beneficial in their own right or in the generation of fermentation products, etc. Therefore, according to a further aspect of the invention there is provided a method of hydrolysis of hemi-celluloses which comprises the digestion of a hemi-cellulose material in an aqueous oxalic acid system subjected to ultrasonic waves, e.g. ultrasound, and separating the desired hydrolysis products, e.g. monosaccharides as hereinbefore described. It will be understood that the hemi-cellulose material may be a mixture of hemi-celluloses materials and may comprise the hemi-cellulose separated from a bulk biomass material or may comprise the biomass material itself.

The ultrasound as a power source may be in the range of from 2 to 10 MHz, for the purposes of the present invention the ultrasound used will generally have a frequency in the range of from 10 to 250 kHz, alternatively, from 20 to 100 kHz. The process liquor or slurry is subject to the operating vicinity of the ultrasonic probe if used, or of an ultrasonic energy transducer, such as a wrap-around ultrasonic energy transducer assembly, if such a configuration is employed. A suitable example of such a device, known in industry and commercially as the Prosonitron™, is documented in WO 00/35579. The ultrasonic energy may be applied continuously or in a discontinuous manner, such as by pulsed application. Any suitable source of ultrasonic irradiation may be used. An ultrasonic probe may, for example, be inserted into a mixing vessel, such as a continuous ultrasonic flow cell, an ultrasonic emitter may be contained in the mixing vessel, or the mixing vessel may be housed in an ultrasonic bath or it may have an ultrasound transducer fixed to the external walls of the mixing vessel. The amplitude and frequency of the ultrasound waves affects the rate of nucleation and crystal growth. The frequency of the ultrasound waves may for example be from 16 kHz to 1 MHz, preferably from 10-500 kHz, more preferably from 10-100 kHz such as at 10, at 20, 40, 60, 80, or 100 kHz or at any frequency therebetween, such as, 30 kHz or 50 kHz.

The ultrasonic irradiation is employed at an amplitude or power density that is appropriate for the production of material for a pre-determined application. For laboratory probe systems with an emitting face of, for example 80 cm$^2$, the amplitude selected may be from about 1-30 µm, typically from 3-20 µm, preferably from 5-10 µm, for example, 6 µm. Probes having a probe face surface area of 8 cm$^2$ and a power requirement of from 5-80 W, provide a power density of from about 0.6-12.5 W/cm$^2$ using amplitude of 2-15 µm. In larger systems, preferably such as those embodied in WO 03/101577, comprising transducers bonded onto the flow cell, for example a 6 liter flow cell, the power density for the transducers employed may be from 10-100 W/L, preferably from 30-80 W/L, and more preferably from 50-75 W/L, for example 60 W/L or 70 W/L. The present invention is particularly suitable for industrial scale production.

The residence time of the mixed components in the ultrasonic flow cell may be preferably greater than 0.1 ms, more preferably greater than 1 ms, more preferably greater than 1 minute, for example between 1 second and 24 hours, more preferably between 1 minute and 6 hours, more preferably between 5 minutes and 1 hour.

The ultrasound source may vary depending, inter alia, upon the nature of the biomass, but we have found that an ultrasound source with an energy output of from 50 to 400 W is desirable, e.g. 100 to 300 W or 150 to 250 W, e.g. 200 W.

The process of the reaction may include an additional energy source, i.e in addition to sonication. A variety of additional energy sources may be utilised, such as thermal energy. However, it is a particular advantage of the present invention that the separation process may be carried out at low temperature, that is, low temperature compared to prior art process. Thus, for example, the prior art process described in the process described in U.S. Pat. No. 5,730,837 is conducted at a temperature of 140° C. and up to as high as 220° C., whereas, by contrast, the process of the present invention may be conducted at a temperature of about 40° C., for example from 30 to 60° C. Therefore, according to the present invention an additional energy source which may be utilised may be microwave energy. Although it is known to use microwave energy in the treatment of biomass materials, the use of microwave in association with sonication is novel per se and is considered within the scope of the present invention.

The process of the present invention may be desirably carried out at atmospheric pressure, however, it is within the scope of the present invention for the reaction to be carried out at elevated pressure. As the pressure is increased, the cavitations may be effected, e.g. decreasing the mechanical benefits of ultrasound in the process. The term "cavitation" is known to the person skilled in the art to mean the formation, growth, and collapse of bubbles or cavities.

After the separation is complete, the phase may be easily separated by the addition of either water or water-immiscible solvent. The lignin present in the water-immiscible solvent, e.g. the ketone, may be isolated by conventional techniques, such as, for example, evaporation of the usually volatile, water-immiscible solvent. The hemi-cellulose and dissolved sugars will generally be in the aqueous or water miscible phase and cellulosic material remaining in an insoluble cake.

The process described herein is advantageous in that, inter alia, a large proportion of the materials employed in the method described herein is recyclable, for example, there may be as much as 95% recovery of the materials e.g. solvents, acid, etc used in the method of the invention. In particular, since, as hereinbefore described, oxalic acid is a solid at room temperature (melting point 189-191° C.) it can therefore be recovered and reused in an efficient and clean manner through simple crystallisation and filtration, or through chromatographic separation.

Thus, according to a further aspect of the invention there is provided lignin, hemi-cellulose and/or cellulose prepared from biomass by the process as hereinbefore described. Although, depending upon the level of acidity, the hemi-cellulose may be fully hydrolysed. In one aspect of the invention there is provided lignin prepared by the process as hereinbefore described. In another aspect of the invention there is provided hemi-cellulose prepared by the process as hereinbefore described. In another aspect of the invention there is provided cellulose prepared by the process as hereinbefore described.

Therefore, the invention further provides lignin prepared from biomass by a method which comprises the steps of:
(i) processing biomass material in an aqueous system in the presence of an oxalic acid catalyst to produce a slurry;
(ii) subjecting the slurry to ultrasound in a pre-treatment step; and
(iii) separating the biomass material into its constituents of lignin, and cellulose, and optionally hemi-cellulose (monosaccharides), and isolating the lignin.

The invention further provides hemi-cellulose prepared from biomass by a method which comprises the steps of:
(i) processing biomass material in an aqueous system in the presence of an oxalic acid catalyst to produce a slurry;
(ii) subjecting the slurry to ultrasound in a pre-treatment step; and
(iii) separating the biomass material into its constituents of lignin, hemi-cellulose (monosaccharides) and cellulose and isolating the hemi-cellulose.

There is especially provided a process for the preparation of fine chemicals from organosolv extracted lignin, e.g. an acidified organosolv, prepared according to the process of the present invention. Acidified organosolv extracted lignin is generally a very pure form of lignin and therefore is especially suitable for use in the preparation of fine chemicals.

In addition or in the alternative the solvent separation process as hereinbefore described may comprise the use of one or more solvent compatible membranes, for example a nanomembrane, which aid the separation of for example, water miscible and water immiscible components. The use of membrane separation may be desirable in that, inter alia, it would minimise or remove the need for the use of certain solvents and especially organic solvents which may be environmentally undesirable.

The process as hereinbefore described may comprise a continuous process or a batch process. For use on a large plant scale a continuous process is preferred.

The invention will now be described by way of example only and with reference to the accompanying tables and Figures in which.

in which.

EXAMPLE 1

TABLE 1

Acidity of acids

| Organic acid | Strength (pKa value) |
| --- | --- |
| Glutamic | 2.1 (weakest) |
| Oxalic | 1.2 |
| Trifluoroacetic | 0.77 |
| Benzenesulfonic | −2.5 |
| Trifluoromethanesulfonic | −13 (strongest) |

EXAMPLE 2

Various ratios of the feed stock and a dilute acid mixture were trialled within the preparation stage to generate slurry of good homogeneity for downstream applications. With a pre-requisite dilute acid mixture comprising 0.1 M of oxalic acid, we found a 1:5 weight based mass ratio of woody saw dust to dilute acid gave a good homogeneous medium. In contrast, a 1:10 ratio of grassy biomass to dilute acid yields a similar result. As expected, wheat and palm frond due to their absorptive nature retain a higher amount of water to that of oak or pine. See Table 2 for further details of accurate weight based input compositions. Note that distilled water has been used throughout with oxalic acid (solid) is mixed with the distilled water prior to addition of biomass. De-oxygenated water is the preferred choice.

TABLE 2

Inlet material compositions

| Inlet material | Overall composition [wt. %] | Overall composition [wt. %] |
| --- | --- | --- |
| Biomass type | Hard/Soft woods | Grasses/cereals/leaves |
| Biomass | 18.31 | 10.07 |

TABLE 2-continued

Inlet material compositions

| Inlet material | Overall composition [wt. %] | Overall composition [wt. %] |
| --- | --- | --- |
| Water | 80.97 | 89.12 |
| Oxalic acid (0.1M) | 0.73 | 0.80 |

Note:
These ratios are true for dried biomass, i.e. biomass without moisture

EXAMPLE 3

The solvents MIBK, EtOH and oxalic acid are to be pre-mixed and added to the blended slurry (which contains the required water content) at a ratio specified in Table 3. This composition conforms to the norm ratio of 1 g biomass to 10 ml organosolv solvents. A brief note on the physical challenges in handling these slurries: at these ratios, the slurries are very fluid and easily transportable. This is especially true for the hard and softwoods. Biomass of a more fibrous nature is more absorbent and therefore the increased solvent ratio is required.

TABLE 3

Inlet material compositions of sonication stage

| Inlet material | Overall composition [wt. %] | Overall composition [wt. %] |
| --- | --- | --- |
| Biomass type | Hard/Soft woods | Grasses/cereals/leaves |
| Blended slurry | 55.26 | 52.88 |
| MIBK | 14.32 | 15.08 |
| EtOH | 30.42 | 32.04 |

EXAMPLE 4

Figure 5:
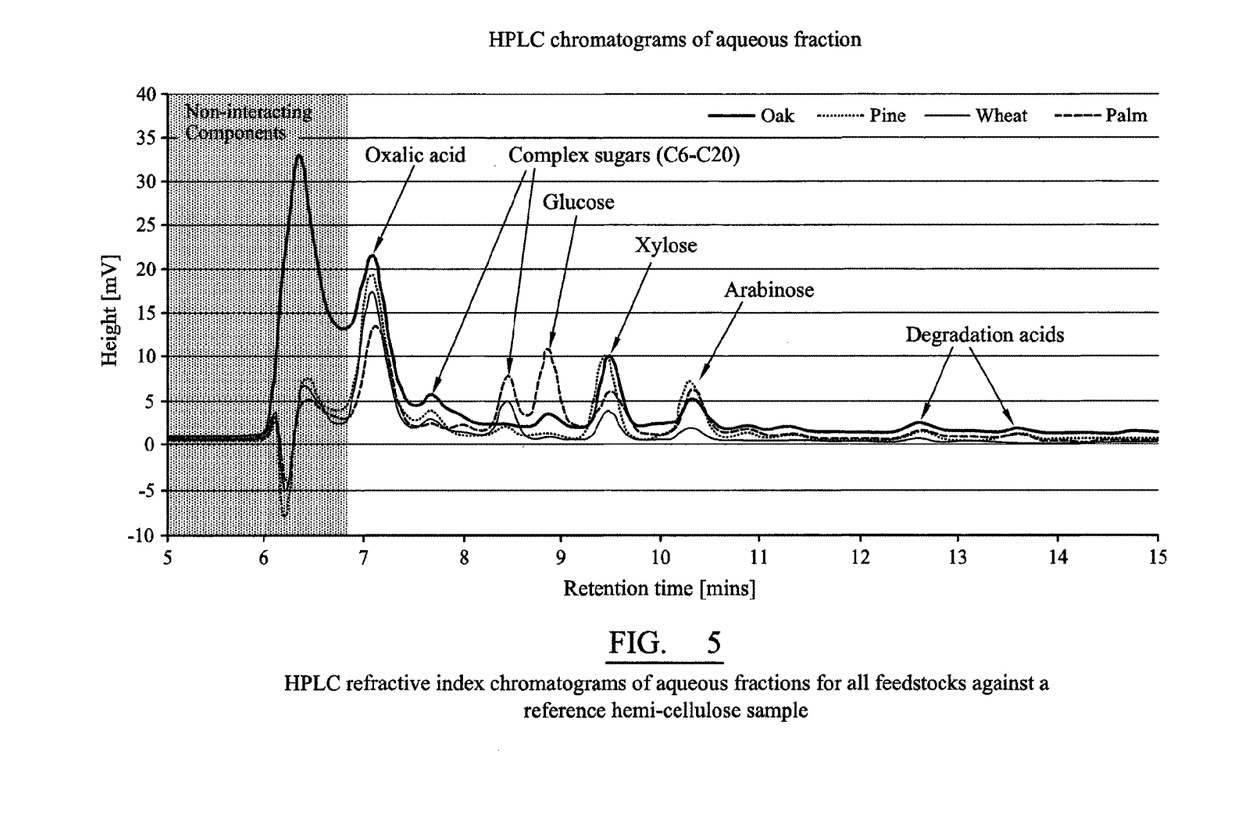
FIG. 5 illustrates the HPLC refractive index chromatograms of aqueous fractions for all feedstocks against a reference hemi-cellulose sample.

Regarding the hemi-cellulose within the aqueous fraction, the ethanol was removed, e.g. on a small scale this may be by evaporation, to yield a concentrated rich solution, although chromatographic separation techniques are preferred. Samples were taken and subjected to HPLC analysis for approximate sugar concentrations (as seen in chromatograms of FIG. 5(a)). The chromatograms reveal the aqueous hemi-cellulose fraction is more complex and may prove more difficult to purify than either the cellulose or lignin fractions. The hemi-cellulose sugars are mixed with the acid promoter as well as traces of acetic acid, other organic acids released during the separation process, EtOH, MIBK, as well as very low molecular weight lignin fragments. Simple removal of water to isolate hemi-cellulose sugars from the aqueous fraction may result in decomposition and low material balance due to acid promoted dehydration and condensation reactions. However, chromatographic separation techniques may prove suitable. In addition to the hemi-cellulose sugars, the aqueous phase contains large amounts of the oxalic acid catalyst (as seen in FIG. 5). A non-optimal technique for recovery is crystallisation. By reducing the volume of the aqueous fraction to say 25 wt. % and cooling it down to 4° C., approximately 85 wt. % of the originally charged oxalic acid crystallized within 15 h and could be recovered by simple filtration with high purity. Chromatographic separation may be of benefit here also.

The HPLC refractive index chromatograms of aqueous fractions for all feedstocks against a reference hemi-cellulose sample are illustrated in FIG. 5.

EXAMPLE 5

Analysing the aqueous fraction of like-for-like oxalic acid and sulphuric acid experiments within the autoclave indicates that the use of a mineral acid aids the release of greater xylose quantity. However, there is also a significant increase in the formation of degradation products, succinic acid and lactic acid in particular than using an organic counterpart.

The invention claimed is:

1. A method of fractionating biomass which comprises a pre-treatment stage and a digestion stage, wherein:
   (a) said pre-treatment stage comprises:
      (i) processing biomass material in an aqueous system by blending the biomass material with a dilute oxalic acid catalyst to produce an acidified slurry;
      (ii) mixing the acidified slurry with an acidified organosolv liquor to make a mixture of acidified slurry and acidified organosolv liquor; and
      (iii) de-aerating the mixture of acidified slurry and acidified organosolv liquor; and
   (b) said digestion stage comprises:
      (iv) sonicating the mixture of acidified slurry and acidified organosolv liquor using ultrasound in the presence of thermal energy to form a digestate; and
      (v) separating the digestate into lignin, hemi-cellulose and cellulose constituents by the addition of water.

2. A method according to claim 1 wherein the concentration of the dilute oxalic acid used in step (i) is from about 0.01 M to about 1 M.

3. A method according to claim 1 wherein the concentration of the dilute oxalic acid used in step (i) is about 0.05M.

4. A method according to claim 1 wherein the concentration of the dilute oxalic acid used in step (i) is about 0.1 M.

5. A method according to claim 1 wherein the concentration of oxalic acid in step (iv) is from about 0.01 M to about 1 M.

6. A method according to claim 1 wherein the concentration of oxalic acid in step (iv) is about 0.05M.

7. A method according to claim 1 wherein the concentration of oxalic acid in step (iv) is about 0.1 M.

8. A method according to claim 1 wherein the biomass comprises hardwood or softwood and the weight-based ratio of the biomass to the dilute oxalic acid used in step (i) is from about 0.1:1 to about 1:10.

9. A method according to claim 1 wherein the biomass comprises hardwood or softwood and the weight-based ratio of the biomass to the dilute oxalic acid used in step (i) is about 1:5.

10. A method according to claim 1 wherein the biomass comprises grasses, cereals or leaves and the weight-based ratio of the biomass to the dilute oxalic acid used in step (i) is from about 1:1 to about 0.1:20.

11. A method according to claim 1 wherein the biomass comprises grasses, cereals or leaves and the weight-based ratio of the biomass to the dilute oxalic acid used in step (i) is about 1:10.

12. A method according to claim 1 wherein the de-aeration of the mixture of acidified slurry and acidified organosolv liquor of step (iii) occurs in an inert atmosphere with sonication.

13. A method according to claim 1 wherein the de-aeration of the mixture of acidified slurry and acidified organosolv liquor of step (iii) occurs in an inert atmosphere without the aid of sonication.

14. A method according to claim 13 wherein the inert atmosphere is nitrogen.

15. A method of fractionating biomass which comprises a pre-treatment stage, a digestion stage, and a separation step wherein:
   (a) said pre-treatment stage comprises:
      (i) processing biomass material in an aqueous system in the presence of a dilute oxalic acid catalyst to produce an acidified slurry;
      (ii) blending the acidified slurry with an acidified organosolv liquor to form a mixture of acidified organosolv liquor and slurry; and
      (iii) de-aerating the acidified organosolv liquor and slurry mixture;
   (b) said digestion stage comprises:
      (iv) subjecting the mixture of acidified organosolv liquor and slurry to ultrasound; and
      (v) de-aerating the mixture of acidified organosolv liquor and slurry; and
   (c) said separation step comprising separating the mixture of acidified organosolv liquor and slurry of the biomass material into its constituents of lignin, monosaccharides and cellulose by the addition of an organosolv reagent comprising a ketone, an alcohol, and dilute aqueous oxalic acid.

16. A method of fractionating biomass which comprises a pre-treatment stage and a digestion stage wherein:
   (a) said pre-treatment stage comprises:
      (i) processing biomass material in an inert atmosphere in an aqueous system in the presence of a dilute oxalic acid catalyst to produce an acidified slurry;
      (ii) blending the acidified slurry with an acidified organosolv liquor; and
      (iii) de-aerating the mixture of acidified slurry and acidified organosolv liquor; and
   (b) said digestion stage comprises:
      (iv) subjecting the mixture of acidified slurry and acidified organosolv liquor to ultrasound to produce a digestate;
      (v) de-aerating the digestate; and
      (vi) separating the digestate into its biomass constituents of lignin, monosaccharides and cellulose.

17. A method of fractionating biomass according to claim 16 which comprises in step (vi) separating the digestate into its biomass constituents of lignin, hemi-cellulose and cellulose by the addition of an organosolv reagent comprising a ketone, an alcohol, and dilute aqueous oxalic acid.

18. A method of fractionating biomass according to claim 16 wherein the inert atmosphere comprises a nitrogen atmosphere.

* * * * *